(12) United States Patent
Tokino et al.

(10) Patent No.: US 6,255,472 B1
(45) Date of Patent: Jul. 3, 2001

(54) ISOLATED NUCLEIC ACID MOLECULE ENCODING A HUMAN SKELETAL MUSCLE-SPECIFIC RECEPTOR

(75) Inventors: Takashi Tokino, Sapporo; Yusuke Nakamura, Yokohama, both of (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/381,681

(22) PCT Filed: Mar. 18, 1998

(86) PCT No.: PCT/JP98/01146

§ 371 Date: Jan. 10, 2000

§ 102(e) Date: Jan. 10, 2000

(87) PCT Pub. No.: WO98/42835

PCT Pub. Date: Oct. 1, 1998

(30) Foreign Application Priority Data

Mar. 26, 1997 (JP) ................................... 9-093044

(51) Int. Cl.[7] .................... C07H 21/04; C12P 21/06; C12N 1/20
(52) U.S. Cl. ................ 536/23.5; 536/24.31; 435/69.1; 435/252.3; 435/254.1; 435/320.1; 435/325; 530/350
(58) Field of Search ................... 536/23.5, 24.31; 435/69.1, 252.3, 254.1, 320.1, 325; 530/350

(56) References Cited

PUBLICATIONS

Collo et al, *J. of Neuroscience*, 16(8):2495–2507 (1996).

Soto et al, *Biochem. and Biophys. Res. Comm.*, 223 (2):456–460 (1996).

Valera et al, *Receptors and Channels, Ch*, Harwood Academic Publishers, 3(4):283–289 (1995).

Seguela et al, *J. of Neuroscience*, US, New York, NY, 16(2):448–455 (1996).

*Primary Examiner*—Karen Cochrane Carlson
*Assistant Examiner*—Stephen Tu
(74) *Attorney, Agent, or Firm*—Sughrue, Mion, Zinn, Macpeak & Seas PLLC

(57) ABSTRACT

Novel human genes usable in gene diagnosis and development of new therapeutic methods are disclosed. Specifically, human genes containing a nucleotide sequence encoding the entirety of or a portion of the amino acid sequence represented by SEQ ID NO:3, in particular, ones which are under the specific transcriptional regulation by a tumor suppressor gene p53.

3 Claims, 11 Drawing Sheets

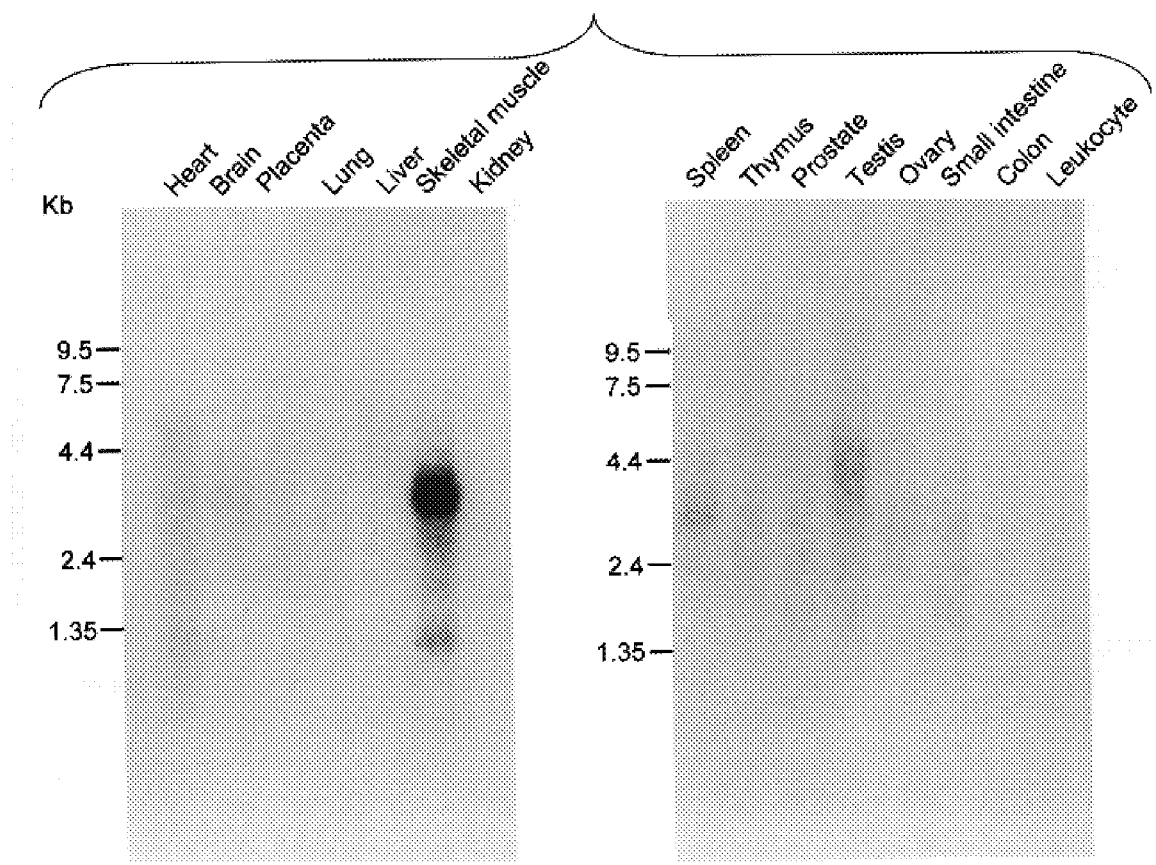

FIG. 3

| Exon | Length (bp) | Coordinates | Splice acceptor | Splice donor |
|---|---|---|---|---|
| 1 | >179 | 1-179 | — | GTG GTA GG /gtaagagag<br>Val Val Gly |
| 2 | 151 | 180-330 | cctccccag/ G TGG GCG<br>Gly Try Ala | CCA CCT CAG/gtggggcc<br>Pro Pro Gln |
| 3 | 72 | 331-402 | gcctcctag/GGA GAG AAC<br>Gly Glu Asn | TGC CCA GAG/gtgagttta<br>Cys Pro Glu |
| 4 | 76 | 403-478 | ccacctcag/CAC CCG TCC<br>His Pro Ser | AGC CAC G /gtaagtgtc<br>Ser His Gly |
| 5 | 94 | 479-572 | gttttctag/ GT GTA AAA<br>Gly Val Lys | GTG CCC TC /gtaagtgtc<br>Val Pro Ser |
| 6 | 81 | 573-653 | cacctgcag/ G AGG CCC<br>Ser Arg Pro | TTC TCT AA /gtaagcaga<br>Phe Ser Lys |
| 7 | 142 | 654-795 | tcctcccag/ G TCC AAT<br>Lys Ser Asn | GCG TTG CTG/gtgggtccc<br>Ala Leu Leu |
| 8 | 110 | 796-905 | tatgtgcag/GGT GGC TCT<br>Gly Gly Ser | AAC TTC AG /gtgaggccc<br>Tyr Asn Arg |
| 9 | 94 | 906-999 | tgcccacag/ G ACA GCC<br>Arg Thr Ala | ACC GGG CAG/gtaggcaca<br>Thr Gly Gln |
| 10 | 66 | 1000-1065 | ctctctcag/GCA AAG<br>Ala Gly Lys | CTG GGC GTG/gtgagtgcg<br>Leu Gly Val |
| 11 | 78 | 1066-1143 | ctctcccag/GTC ACC TTT<br>Val Thr Phe | TAT GAG GAG/gtgagctga<br>Tyr Glu Glu |
| 12 | >2409 | 1144-3552 | catctgcag/GCC AAG GCC<br>Ala Lys Ala | — |

FIG. 5

```
                                                                M1
P2XM   M--GSPGATTGWGLLDYKTEKYVMTRNWRVGALQRLLQFGIVVYVGWALLAKKGYQERDLEPQFSIITKLKG------VSVTQIKELGNRLWDVADFVK    92
P2X1   M-ARRLQDELSAFFFEYDTPRMVLVRNKKVGVIFRLIQLIVLIYVIGWVFVYEKGYQTSSDL-ISSVSVKLKG------LAVTQLQGLGPQVWDVADYVF    92
P2X2   M-VRRLARGCWSAFWDYETPKVIVRNRRLGFVHRMVQLLILLLYFVWYVFIVQKSYQDSETGPESSIITKVKG------ITMSEDKVWDVEEYVK       88
P2X3   M------NCISDFFTYETTKSVVKSWTIGIINRAVQLLIISYFVGWVFLHEKAYQVRDTAIESSVVTKVKG------FGRYANRVMDVSDYYT         82
P2X4   MA--GCCSVLGSFLFEYDTPRIVLIRSRKVGLMNRAVQLILLAYVIGWVFVWEKGYQETDSV-VSSVTTKAKG------VAVTNTSQLGFRIWDVADYVI    91
P2X5   M-GQAAWKGFVLSLFDYKTAKFVVAKSKKVGLLYRVLQLILILLWFLIKKSYQDIDTSLQSAVVTKVKG------VAYTNTTMLGERLWDVADFVI       93
P2X6   MASAVAAALVSWGFLDYKTEKYVMTRNCWGI SQRLLQLGVVVYIGWALLAKKGYQEWDMDPQISVITKLKG------VSVTQVKELEKRLWDVADFVR    94
P2X7   M-----PACCSWNDVFQYETNKVTRIQSVNYGTIKWILHMTVFSYV-SFALMSDKLYQRKEPL-ISSVHTKVKGVAEVTENVTEGGVTKLVHGIFDTADYT 94

*
P2XM   PPQGENVFFLVTNFLVTPAQVQGRCPEHPSVPLANCWVDEDCPEGEGGTHSHGVKTGQCVV-FNGTHRTCEIWSWCPVESG-VVPSRPLLAQNFTLFI    190
P2X1   PAHGDSSFVVMTNFIVTPAQQTQGHCAE--NPEGGICQDDSGCTPGKAERKAQGIRTGNCVP-FNGTVKTCEIFGWCPVEVDDKIPSPALLREAENFTLFI 189
P2X2   PPEGGSVVSIITRIEVTPSQTLGTCPESMRVHSSTCHSDDDCIAGQLDMQGNGIRTGHCVPYYHGDSKTCEVSAWCPVEDG-TSDNHFLGKMAPNFTILI 187
P2X3   PPQGTSVFVIITKMIVTENQMQGFCPE----GPERFPGGGILITGRCVN-YSSVLRTCEIQGWCPTEVD--TVEMPIMEAENFTIFI              175
P2X4   PAQENSLFIMTNMIVTVNQTQSTCPE--IPDKTSICNSDADCTPGLRDTHSSGVATGRCVP-FNESVKTCEVAAWCPVENDVGVPTPAFLKAAENFTLLV 189
P2X5   PSQGENVFFVVTNLIVTPNORQIGAEREGIPDGECSEDDDCHAGESVVAGHGLKTGRCLRVGNSTRGTCEIFAWCPVETK-SMPTDPLLKDAESFTISI   192
P2X6   PSQGENVFFLVTMINFLVTPAQVQGRCPEHPSVPLANCWADEDCPEGEMGTYSHGIKTGQCVA-FNGTHRTCEIWSWCPVESS-AVPRKPLLAQAKNFTLFI 192
P2X7   LPLQGNSFFVMTNYLKSEGQEQKLCPEYPS-RGKQCHSDQGCIKGWMDPQSKGIQTGRCIP-YDQKRKTCEIFAWCPAEEGKEAPRPALLRSAENFTVLI  192

*
P2XM   KNTVTFSKFENFSKSNALETWDPTYFKHCRYEPQFSPYCPVFRIGDLVAKAGGTFEDLALLGGSVGIRVHWDCDLDTGDSGCWMPHYSFQLQEK------  282
P2X1   KNSISFPRFKVNRRNLVEEVNGTYMKKCLYHKIQHPLCPVFNLGYVVRESGQDFRSLAEKGGVVGITIDWKCDLDWHVRHCKPIYQFHGLYG---EKNLS  286
P2X2   KNSIHYPKFKFSKGNIAS-QKSDYLKHCTFDQDSDPYCPIFRLGFIVEKAGENFTELAHKGGVIGVI INWNCDLDLSESECNPKYSFRRLDP--KYDPAS 284
P2X3   KNSIRFPLENFEKGNLLPNLTDKDIKRCRFHPEKAPFCPILRVGDVVKFAGQDFAKLARTGGVLGIKIGWVCDLDKAWDQCIPKYSFTRLDGVSEKSSVS  275
P2X4   KNNIWYPKFNFSKRNILPNITTSYLKSCIYNAQTDPFCPIFRLGTIVEDAGHSFQEMAVEGGIMGIQIKWDCNLDRAASLCLPRYSFRRLDTRDLEHNVS  289
P2X5   KNFIRFPKFNFSKANVLETDNKHFLKTCHF-SSTNLYCPIFRLGSIVRWAGADFQDIALKGGVIGLYIEWDCDLDKAASKCNPHYYENRLDN-KHTHSIS  290
P2X6   KNTVTFNKFNFSRTNALDTWDNTYFKYCLYDSLSSPYCPVFRIGDLVAMTGGDFEDIAVQGGIMGIEIYWDCNLDSWSHRCQPKYSFRRLDDKYTNESLF 284
P2X7   KNNIDFPGHNYTTRNILP---GMNISCTFHKTWNPQCEIFRLGDIFQEIGENFTEVAVQGGIMGIEIYWDCNLDSWSHRCQPKYSFRRLDDKYTNESLF  288
```

FIG. 6

```
                        H5                                              M2
P2XM  -SYNFRTATHWWEQPGVEARTLLKLYGIRFDILVTGQAGKFGLIPTAVTLGTGAAWLGVTFFQDLLLLYVDREAHFYWRTKYEEAKAPKATANSVWREL    381
P2X1  PGFNFRFARHFVQ-NGTNRRHLFKVFGIHFDILVTGGKAGKFDIIPTMTTIGSGIGIFGVATVLCDLLLLHILPKRHYYKQKKFKYAEDMGPGEGEHDPVA    385
P2X2  SGINFRFAKYYKINGTTTTRTLIKAYGIRIDVIVHGQAGKFSLIPTIINLATALTSIGVGSFLCDWILLTFMNKNKLYSHKKFDKVRTPKHPSSRWPVTL    384
P2X3  PGINFRFAKYYKDSKGVEYRTLLKAFGIRFDVIVYGNAGKFNIIPTIISSVAAFTSVGVGTVLCDIILNFLKGADHYKARKFEEVTETTLKGTASTNPV    375
P2X4  PGINFRFAKYYRDLAGKEQRTLIKAYGIRFDIIVFGKAGKFDIIPTMINVGSLALLGVATVLCDVIVLYCMKKKYYYRDKKYKYVEDYEQLSGEMNQ     388
P2X5  SGINFRFARYYRDPNGVEFRDLMKAYGIRFDVIVNGKAGKFSIIPTVINIGSGLAIMGAGAFFCDLVLIYLIRKSEFYRDKFEKVRGQKEDANVEVEAN    390
P2X6  -GINFRTANYWWAASGVESRSILKLYGIRFDIIVTGQAGKFALIPTAITVTGAAWLGMVTFLCDLLLLYVDREAGFYWRTKYEEARAPKATTNSA       379
P2X7  PGINFRYAKYYKEN-GMEKRTLIKAFGVRFDIIEAFGTGGKFDIIQLVVYIGSTLSYFGLATV-CIDLIINTYASTCCRSRVYPSCKCCEPCAVNEYYYRK  386

P2XM  ALASQARLAECLRRSSAPAPTATAAGSQTQTPGWPCPSSDTHLPTHSGSL                                                   431
P2X1  TSSTLGLQENMRTS                                                                                      399
P2X2  ALVLGQIPPPPSHYSQDQPPSPPSGEGPTLGEAELPLAVQSPRPCSISALTEQVVDTLGQHMGQRPPVPEPSQQDSTSTDPKGLAQL             472
P2X3  FASDQATVEKQSTDSGAYSIGH                                                                              397
P2X5  EMEQERPEDEPLERVRQDEQSQELAQSGRKQNSNCQVLLEPARFGLRENAIVNVKQSQILHPVKT                                   455
P2X7  KCEPIVEPKPTLKYVSFVDEPHIWMVDQQLLGKSLQDVKGQEVPRPQTDFLELSRLSLHHSPPIPGQPEEMQLLQIEAVPRSRDSPDWCQCGNCLPSQ  486

P2X7  LPENRRALEELCCRRKPGQCITTSELFSKIVLSREALQLLLLYQEPLLALEGEAINSKLRHCAYRSYATWRFVSQDMADFAILPSCCRWKIRKEFPKTQG  586

P2X7  QYSGFKYPY                                                                                           595
```

ISOLATED NUCLEIC ACID MOLECULE ENCODING A HUMAN SKELETAL MUSCLE-SPECIFIC RECEPTOR

TECHNICAL FIELD

The present invention relates to genes which are useful for prevention of human diseases and for establishing guidelines for diagnosis and therapeutic treatment, and more particularly, to human genes which are transcriptionally regulated specifically by a tumor suppressor gene p53, as well as to genes which can feasibly be used for gene diagnosis and development of new therapeutic methods.

BACKGROUND ART

Among genetic alterations found in human cancer, mutations of a tumor suppressor gene p53 are most prevalently seen, and thus the p53 gene is believed to be one of the most important genes relevant to tumorigenicity in the human body (Hollstein M. et al., Science (Washington DC), 253: 49–53, 1991). The p53 gene functions as a transcription factor (Vogelstein B., et al., Cell, 70: 523–526, 1992), and it has been confirmed that, upon its binding to a specific DNA sequence, p53 can activate various genes, including p21/WAF1, MDM2, GADD45, BAX, cyclin G, IGF-BP3, PCNA, and GML (EI-Deiry, W. S., et al., Cell, 75: 817–825, 1993; Wu X., et al., Genes Dev., 7: 1126–1132, 1993; Kastan M. B., et al., Cell, 71: 587–597, 1992; Miyashita T., et al., Cell, 80: 293–299, 1995; Okamoto K., et al., EMBO. J., 13: 4816–4822, 1994; Buckbinder L., et al., Nature, 377: 646–649, 1995; Morris G. E., et al., Proc. Natl. Acad. Sci. USA, 93: 885–899, 1996; and Furuhata T., et. al., Oncogene, 13: 1965–1970, 1996). Among these genes, p21/WAF1, BAX, and GML are thought to be major factors involving cell cycle arrest and apoptosis mediated through p53, whereas GADD45 plays an important role in DNA repair.

Thus, identification of genes regulated by p53 is vital for understanding biological and physiological functions of p53. Furthermore, identification of p53-target genes and elucidation of their functions are eagerly awaited not only by cancer researchers but also by researchers who hope to develop new methods of diagnosis and treatment of cancer through use of such target genes.

It should be noted that the present inventors have already designed and established a method of finding candidates for p53-target genes in the vicinity of functional p53-binding sites (p53-tagged sites) in the human genome. Using the method, the present inventors have successfully demonstrated isolation of the GML gene, whose expression is believed to be positively correlated with sensitivity to anti-cancer drugs (Furuhata T., et al., Oncogene, 13: 1965–1970, 1996).

An object of the present invention is to provide the demanded information which is vitally important to the above fields; that is, to provide information which can enable finding and identification of target genes for the tumor suppressor gene p53 (p53-target genes) or p53-inducible genes, i.e. novel human genes whose expressions fall under specific transcriptional regulation by p53.

DISCLOSURE OF THE INVENTION

Upon cloning functional p53-tagged sites from the human genome, the present inventors have isolated a novel human gene which can be induced by wild-type p53, and have further demonstrated that the isolated novel gene satisfies the above object, thus successfully completing the invention.

Accordingly, the present invention provides a human gene comprising a nucleotide sequence encoding the entirety of or a portion of the amino acid sequence shown in SEQ ID NO:3, and, in particular, a gene which comprises the entirety of or a portion of the nucleotide sequence shown in SEQ ID NO:1.

BRIEF DESCRIPTION OF THE DRAWINGS

FIG. 2 is a photo showing the results of northern blot analysis of P2XM in various types of human tissue.

FIGS. 3 and 4 depict the genomic structure of the P2XM gene. FIG. 3 shows nucleotide sequences of exon-intron boundaries of the 191 gene;

FIGS. 5 and 6 depict amino acid sequences of various P2X receptors.

BEST MODE FOR CARRYING OUT THE INVENTION

Figure 1:
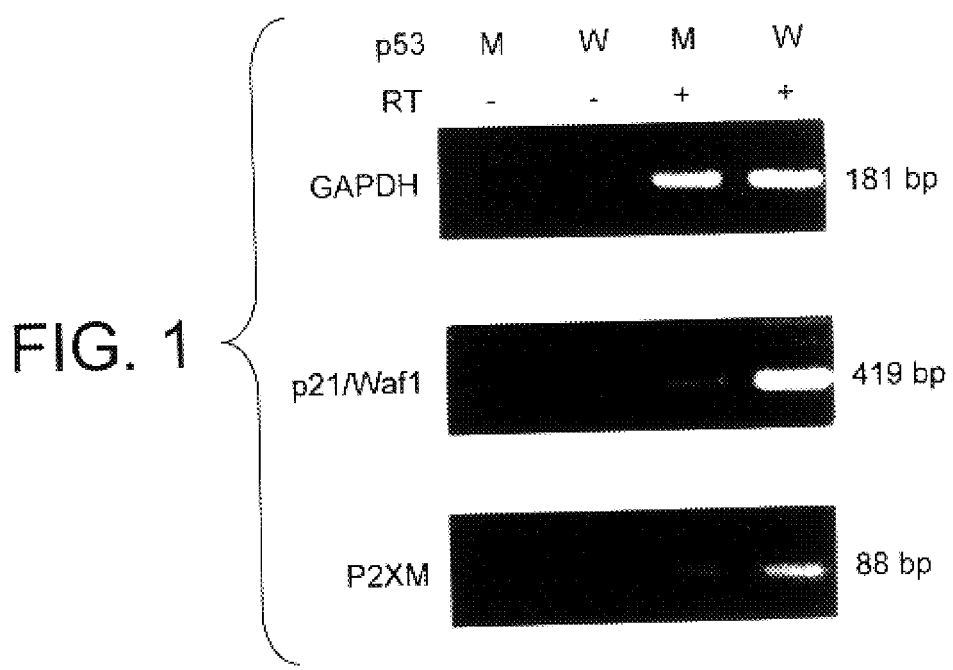
FIG. 1 is a photo showing the results of RT-PCR analysis of expression of p53-inducible mRNA in a colon cancer cell line SW480 whose genome has lost the wild-type p53 allele. This analysts was carried out in order to examine induction of P2XM gene expression by wild-type p53.

Hereafter, the usage of abbreviations of amino acids, peptides, nucleotide sequences, nucleic acids, etc. used in the present specification will follow the guidelines of IUPAC, IUB, and "The guidelines for preparation of specifications including nucleotide sequences or amino acid sequences" edited by the Japanese Patent Office, as well as guidelines customarily followed in the corresponding fields.

Examples of the gene of the present invention include genes deduced from the DNA sequence of a clone termed "P2XM," which will be described later in the Example section, and whose nucleotide sequence is shown in the sequence list attached hereto.

As shown in SEQ ID NO:1, the gene of the present invention is shown in a nucleotide sequence of a single-strand DNA. However, the present invention includes not only the nucleotide sequence of a single-strand DNA, but also its complementary DNA sequence, as well as components containing both. Further, the gene sequence of the present invention shown in SEQ ID NO:1 is an example combination of various codons encoding an amino acid residue, and thus the gene of the present invention should not be construed as being limited thereto; for example, the gene of the present invention may also include a nucleotide sequence resulting from an arbitrary combination of codons encoding an amino acid residue. Construction of such a combination can be accomplished by use of conventional methods; for example, by use of codon usage frequencies in an employed host (Nucleic Acid Res., 9: 43–74, 1981).

Further, the gene of present invention also includes the DNA nucleotide sequences encoding proteins having similar functions and exhibiting similar effects, of which some amino acid residue(s) or part(s) of the amino acid sequences described above are altered by replacement, deletion, addition, etc. Syntheses or alterations (mutations) of such polypeptides can occur spontaneously or can be induced by posttranscriptional modifications or by use of genetic engineering techniques. In the latter case, in order to obtain such mutated DNA, a natural gene, for example, (such as a gene according to the embodiment of the present invention) can be modified by, for example, site-specific mutagenesis (Methods in Enzymology, 154: p. 350, 367–382, 1987; ibid., 100: p. 468, 1983; Nucleic Acid Res., 12: p. 9441, 1984; "Zoku-Seikagaku Jikken Koza 1, 'Idenshi Kenkyuho II'" edited by the Japanese Biochemical Society: p. 105, 1986) or by means of chemical synthesis in accordance with the phosphotriester method or the phosphoramidite method (J. Am. Chem. Soc., 89: p. 4801, 1967; ibid., 91: p. 3350, 1969; Science, 150: p. 178, 1968; Tetrahedron Lett., 22: p. 1859, 1981; ibid., 24: p. 245, 1983) or by combined use of the methods.

The gene shown in SEQ ID NO:1 according to the present invention is transcriptionally regulated specifically by p53; and its expression is activated in vivo by p53 and is thought to play a role in tumor suppression. Thus, the in vivo gene therapy carried out by means of expressing the gene of the present invention or in vivo administration of the gene product could be very useful for cancer prevention as well as for cancer treatment. In particular, for treatment of individuals suffering from the hereditary cancer-prone Li-Fraumeni syndrome, or LOH of p53 gene, or who are destined to get cancer due to loss of the tumor-suppressor function of p53 as is the case of various cancers accompanying mutations of p53, use of the gene of the present invention or a product thereof would be favored.

It should be pointed out that the above-mentioned gene therapy employing the gene of the present invention or a gene product thereof need not always employ the entire gene of the present invention or its entire encoded product; that is, the entire DNA nucleotide sequence or its entire encoded amino acid sequence may not be necessary for such treatment, but instead the above-mentioned modified genes or sequences of portions of the gene or their encoded products can be favorably employed, so long as they are capable of fulfilling the same basic function fulfilled by the gene described in SEQ ID NO:1.

Through use of the gene of the present invention; for example, by introducing the gene into a vector of a certain microorganism and subsequent culturing of the resultant transformants, p53-related proteins encoded by any of the various genes mentioned above can be easily and steadily manufactured.

Further, employment of various proteins synthesized from use of the gene of the present invention enables synthesis of their corresponding specific antibodies. Here, to obtain such antibodies, component proteins used as antigens can be produced on a large scale by use of the above-mentioned genetic engineering techniques; thus, either polyclonal or monoclonal antibodies can be raised, and the antibodies can then be used advantageously for purification, measurement, identification, etc. of the corresponding proteins.

On the basis of the disclosed sequence information of the present invention, the gene of the present invention can be easily manufactured by use of general genetic engineering techniques (see, for example, Molecular Cloning 2nd Ed., Cold Spring Harbor Laboratory Press (1989); "Zoku-Seikagaku Jikken Koza 'Idenshi Kenkyuho I, II, and III'" edited by the Japanese Biochemical Society, 1986).

For example, from a human cDNA library (prepared in accordance with conventional methods and from appropriate cells expressing the corresponding genes), a desired clone can be selected by use of appropriate probes or antibodies specific for the gene of the present invention or its encoded protein (Proc. Natl. Acad. Sci. USA, 78: 6613, 1981; Science, 222: 778, 1983, etc.).

Here, as such expressing cells used for cDNA preparation, various types of cells, tissue, and their deriving cultured cells capable of expressing target genes are exemplified. Preparation of total RNA from these cells, isolation and purification of mRNA, subsequent conversion of mRNA into cDNA (synthesis of cDNA), and cDNA cloning can be carried out by use of conventional methods. Further, various cDNA libraries are commercially available. For cloning the gene of the present invention, various types of cDNA libraries available from Clontech Lab. Inc. and other commercial enterprises can be used, for example.

Screening of the gene of the present invention from a cDNA library can be carried out by use of a conventional method as described above. Examples of such screening methods include the immunological method, with which a corresponding cDNA clone is selected by screening proteins synthesized from cDNAs by use of specific antibodies against the protein; the plaque hybridization method and the colony hybridization method, wherewith a probe capable of binding specifically to the corresponding targeted DNA sequence is employed; and combinations of these methods. Concerning the above-mentioned probes, DNA sequences, etc. which are chemically synthesized based on DNA sequence information of the gene of the present invention are typically used. Needless to say, the entirety of the gene of the present invention may be used, or fragments thereof may be used.

Moreover, based on partial amino acid sequence information of an extracted natural product that has been isolated and purified from various types of cells or tissue, sense primers as well as anti-sense primers can be synthesized and then used as probes for screening.

To obtain the gene of the present invention, amplification of DNA or RNA of the gene with PCR can be advantageously carried out (Science, 230: 1350–1354, 1985). In particular, when a complete full-length cDNA cannot be obtained from a cDNA library, RACE methods may be advantageously used (RACE: rapid amplification of cDNA ends; Experimental Medicine, 12(6): 35–38, 1994); particularly the 5'-RACE method (Frohman M. A., et al., Proc. Natl. Acad. Sci. USA, 8: 8998–9002, 1988). Primers used for carrying out PCR can be properly designed on the basis of the sequence information of the gene of the present invention, which is clarified by the present invention, and can be synthesized by use of a conventional method.

Isolation and purification of the amplified fragments of the DNA or RNA can be carried out by conventional methods, as mentioned above, such as by gel electrophoresis.

Further, nucleotide sequencing of the gene of the present invention or its various DNA fragments as obtained above can be carried out by use of a conventional method, such as the dideoxy method (Proc. Natl. Acad. Sci. USA, 74: 5463–5467, 1977) or the Maxam-Gilbert method (Methods in Enzymology, 65: 499, 1980). Such DNA sequencing can also be easily performed by use of a commercially available sequencing kit.

Various recombinant proteins can be obtained through use of conventional gene recombination techniques and the gene of the present invention (for gene recombination techniques, see, for example, Science, 224: p. 1431, 1984; Biochem. Biophys. Res. Comm., 130: p. 692, 1985; Proc. Natl. Acad. Sci. USA, 80: p. 5990, 1983; and the previously quoted references). In more detail, in order to manufacture the proteins, recombinant DNA constructs capable of being expressed in host cells are first obtained from the gene of the present invention, the DNA constructs are subsequently introduced into host cells for transformation, and resultant transformants are then cultured.

Here, as host cells, either eukaryotic cells or prokaryotic cells can be used. Eukaryotic cells include vertebrate and yeast cells. Vertebrate cells such as COS cells originating form monkey cells (Cell, 23: 175–182, 1981), or Chinese hamster ovarian cells and their dihydro-folate reductase-deficient cell line (Proc. Natl. Acad. Sci. USA, 77: 4216–4220, 1980) are very often used, but the host cells are not limited to these examples.

As an expression vector used for vertebrates, there may be used one that typically contains a promoter located upstream of the gene to be expressed, RNA splicing sites, a polyadenylation site, a transcription terminating sequence, etc. If necessary, the vector may further have multiple replication sites, as exemplified by pSV2dhfr, etc. carrying the SV40 early promoter (Mol. Cell. Biol., 1: 854, 1981). In the case of eukaryotic microorganisms, yeast is often used; in particular, yeast belonging to the Saccharomyces genus is preferably used. Examples of an expression vector for the eukaryotic microorganisms include pAM82 carrying the promoter of the acid phosphatase gene (Proc. Natl. Acad. Sci. USA, 80: 1–5, 1983). Also, prokaryotic gene-fusion vectors are preferable examples of an expression vector for the gene of the present invention. Specific examples of such vectors include pGEX-2TK and pGEX-4T-2, each carrying the GST domain having a molecular weight of 2600 and derived from S. japonicum.

As host cells for prokaryotic organisms, in general, Escherichia coli and Bacillus subtilis are generally used. In these host cells, for example, plasmid expression vectors capable of replicating in the host cells are preferred. Expression of the gene Is preferably carried out by use of a vector that carries a promoter and the SD (Shine-Dalgarno) nucleotide sequence, both of which are required for expression of the gene of the present invention and must be located upstream of the expressing gene. Moreover, each carries an initiation codon (for example, ATG) which is required for initiation of protein synthesis. In the above case of Escherichia coli, Escherichia coli K12 is often used; and as a vector, pBR322 and its improved types of modified vectors are usually used. However, these are nonlimiting examples; and various types of known bacterial strains and vectors can also be used. Examples of the promoter which may be used include tryptophan (trp) promoter, lpp promoter, lac promoter, and PL/PR promoter.

Concerning the methods for introducing and the methods for transforming the thus-obtained recombinant DNA, various general methods may be used. The resultant transformants can be cultured by use of a conventional method; and through cultivation, the protein encoded by the gene of the present invention is synthesized and expressed. Various types of conventionally used media for culturing the host cells can be appropriately used as the culture medium for the transformants; and the transformants can be cultured under the same culture conditions optimally employed for growth of the host cells.

By using the above-mentioned methods, the target recombinant protein can be expressed, produced, and accumulated inside the cell or on cell membrane, or can be secreted outside the cell.

Each recombinant protein can be separated and purified, as desired, by use of various separation techniques selected in accordance with the physical and chemical nature of the recombinant protein (see, for example, "Biochemical Data book II" 1175–1259, 1st printing, 1st Edition, Jun. 23, 1980, published by Tokyo Kagaku Dojin; Biochemistry, 25(25): 8274–8277, 1986; Eur. J. Biochem., 163: 313–321, 1987). Specific examples of such methods include typical reconstitution treatment; a salting-out method employing protein-precipitation reagents; a centrifugation separation method; an osmotic shock method; an ultrasonic disruption method; an ultrafiltration method; various liquid chromatography techniques, including molecular sieve chromatography (gel filtration), adsorption chromatography, ion exchange chromatography, and high performance liquid chromatography (HPLC); dialysis; and various combinations of these methods. Among these methods, most preferred is affinity column chromatography employing a column to which appropriate desired proteins are bound.

Further, on the basis of the sequence information of the gene of the present invention; for example, by use of a portion of or the entirety of the nucleotide sequence of the gene, expression levels of the gene of the present invention can be determined in various types of human tissue. This can be satisfactorily accomplished by means of a conventional method; for example, by carrying out RNA amplification by means of RT-PCR (reverse transcribed-polymerase chain reaction: Kawasaki E. S., et al., "Amplification of RNA. In PCR Protocol, A Guide to Methods and Applications", Academic Press, Inc., San Diego, 21–27, 1991), or by carrying out northern blotting analysis (Molecular Cloning, Cold Spring Harbor Laboratory, 1989).

It should be pointed out that the above-mentioned PCR can employ any set of primers, so long as they are specific to the gene of the present invention and can amplify the gene of the present invention alone in a selective manner. Thus, the primer sequences can be appropriately set on the basis of the sequence information of the gene of the present invention. Usually, according to conventional methods, one primer can have a partial sequence consisting of 20–30 nucleotides.

Thus, the present invention also provides primers and/or probes useful for detection of characteristics of these novel human genes.

EXAMPLES

The present invention will next be described in detail by way of examples.

EXAMPLE 1

(1) Screening cosmid libraries

A p53-tagged site (clone p53-191) has been identified by use of the method of Tokino, et al. (Tokino T., et al., Hum. Mol. Gene. 3: 1537–1542, 1994). By use of a [$^{32}$P]-labeled probe containing the p53-tagged site, a cosmid cDNA library prepared from human peripheral lymphocytes was screened. The obtained cosmid p53-cos191 was digested with EcoRI; then the resultant EcoRI fragment was subcloned into pBluescriptIISK (−) (Stratagene); and its DNA sequence was determined by use of a ABI377 DNA sequencer and a DNA sequencing kit (Taq DyeDeoxy Terminator Cycle Sequencing Kit; ABI).

(2) CDNA cloning

In order to isolate a gene present in cosmid p53-cos191, both exon amplification and RACE methods were carried out.

Cosmid p53-cos191 was digested with BamH I and Bgl II; then the resultant digested fragment was inserted into the BamH I site of an exon-trapping vector pSPL3 (Gibco-BRL); and the resultant DNA was introduced to COS7 cells by use of LipofectACE (Gibco-BRL). After cultivation for 24 hr, total RNA was prepared with TRIZOL (Gibco-BRL). The first stranded cDNA fragment synthesized, as well as spliced fragments, was subjected to PCR amplification according to the method of North et al. (North M. A., et al., Mamm. Genome, 4: 466–474, 1993). The resultant cDNA fragments were then subcloned into pBluescriptIISK (−), followed by DNA sequencing by use of a T3 or T7 primer, as mentioned above. As one of the candidates, a sequence 191E1 was subjected to 5′- and 3′-RACE by use of templates of poly(A)+ RNA in skeletal muscle with a cDNA amplification kit (Marathon cDNA amplification kit; Clontech).

(3) RT-PCR analysis

Transient introduction of p53 expression vector, p53-wt or p53-273 DNA (Kern S. E., et al., Science (Washington DC), 256: 827–830, 1992) to a colon cancer cell line SW480, as well as cDNA preparation, was carried out in accordance with the report of Furuhata et al. (Furuhata T., et al., Oncogene, 13: 1965–1970, 1996). Total RNA was reverse-transcribed by use of SuperscriptII (Gibco-BRL). Semi-quantitative comparisons between the cDNA samples were carried out during the exponentially increasing phase at cycles 20–30 of RT-PCR. In this experiment, each PCR reaction was carried out by use of cDNA generated from 200 ng of total RNA. For this, the PCR reaction mixture described in literature was used (Han H-J., et al., Hum. Mol. Genet., 4: 237–242, 1995); and the reaction was carried out at 94° C. for 2 min at the initial denaturation step, followed by 30 cycles for 191E1 or 25 cycles for p21/WAF1, and GAPDH with a cycling step of 94° C. for 30 sec, 55–60° C. for 30 sec, and 72° C. for 1 min (GeneAmp PCR system 9600; Perkin Elmer). The nucleotide sequences of primers used are shown in Table 1.

TABLE 1

| Primer | Nucleotide sequence |
| --- | --- |
| (191E1) | |
| E1S2 | 5′-AGCCACTCACTGGTGGGA-3′ (SEQ ID NO:4) |
| E1A2 | 5′-CCCGGTGACGAGGATGTCGA-3′ (SEQ ID NO:5) |
| (p21/WAF1) | |
| W1S | 5′-GTTCCTTGTGGAGCCGGAGC-3′ (SEQ ID NO:6) |
| W2A | 5′-GGTACAAGACAGTGACAGGTC-3′ (SEQ ID NO:7) |
| (GAPGH) | |
| HGS | 5′-CAACTACATGGTTTACATGTTC-3′ (SEQ ID NO:8) |
| HGA | 5′-GCCAGTGGACTCCACGAC-3′ (SEQ ID NO:9) |

The amplified cDNA was separated on a 3% NuSieveGTG (2:1) agarose gel.

(4) Northern blot analysis

A northern blot carrying poly(A)+ RNA samples derived from various normal human tissue (Clontech) was subjected to hybridization with a [$^{32}$P]-randomly primed probe corresponding to a region of the gene of the present invention at nucleotide positions 909–1583. The blot was washed at 50° C. with a solution containing 0.1XSSC and 0.1% SDS, followed by autoradiography at −80° C. for 24 h.

(5) FISH

FISH was carried out according to the method of Inazawa, et al. (Inazawa J., et al., Genomics, 17: 153–162, 1993). Human metaphase chromosomes were prepared through a conventional method (thymidine synchronization/bromodeoxyuridine release technique). Prior to hybridization, the metaphase cells were subjected to staining with Hoechst 33258 and UV-irradiation. The cosmid clone p53-cos191 was nick-translated and labeled with biotin-16-dUTP, and used for hybridization to denatured metaphase chromosomes. In order to remove noise signals generated by scattered repeat sequences such as Alu repeats, the chromosomal in situ suppression technique was used. Hybridized signals were detected by use of FITC-avidin, and their precise locations were determined by visualization of replication-G bands.

(6) Homology search

Comparisons of DNA sequences were carried out by use of the FASTA program for homology search of data bases (non-redundant nucleic sequence database and non-redundant protein sequence database; Human Genome Center, Institute of Medical Science, Tokyo University).

(7) Results (I) Cloning of p53-inducible genes

By means of screening a cosmid human genome library with a probe of clone P53-191, which was one of the p53-tagged sites, cosmid clone: p53-cos191 was obtained. In order to examine whether the sequence derived from the cosmid was regulated transcriptionally by p53, RT-PCR analysis was carried out. For this RT-PCR assay, expression vector DNA carrying wt p53 or a mutant p53 cDNA was transiently introduced to SW480 cells (SW-480-wt53 or SW-480-mt53, respectively), and RNA prepared from these cells were used as a template. When one of the candidate sequences, 191E1, was tested, expression of 191E1 increased remarkably in SW-480-wt53 (wild type) as compared with that in SW480-mt53 (mutant type) (see FIG. 1), thus implying that 191E1 expression was induced by wild-type p53.

It should be pointed out that the colon cancer cell line SW480 cells lacked the wild-type p53 allele. By use of the cell line, p53-inducible mRNA expression was analyzed by RT-PCR. The obtained results are shown in the photo of FIG. 1.

Thus, expression of P2XM gene was confirmed by RT-PCR amplification following transient transformation of SW480 cells with SW480-wt53 (W) or SW480-mt53 (M). RNA samples were subjected to reverse transcription in the presence (+) or absence (−) of reverse transcriptase (RT). For this RT-PCR analysis, amounts of the template samples were normalized with respect to amplified amounts of the GAPDH transcript; and the two samples showed approximately the same level of GAPDH signals.

Next, by use of 191E1 as a probe, cDNA screening and subsequent 5′- and 3′-RACE were carried out. Thus, the cDNA consisting of 3552 bp was isolated. The CDNA termed P2XM contained an open reading frame of 1293 bp encoding a protein of 431 amino acid residues. The entire DNA sequence is shown in SEQ ID NO:2. The coding region of the cDNA P2XM was present at nucleotide positions 46–1338; potential transmembrane domains (M1 and M2) were at amino acid residues 33–49 and 324–344, respectively; and a segment (H) homologous to voltage-gated K+ channel H5 was present at amino acid residues 306–319.

Northern blot analysis using the cDNA as a probe showed the 3.6-kb transcript in skeletal muscle (see FIG. 2). Thus, the cDNA appeared to contain almost the entire transcript. FIG. 2 is a photo showing the results of northern blot analysis of P2XM expression in various human tissue. In this experiment, a blot with poly(A)$^+$ RNA (2 μg/lane) prepared from various tissue (the heart, brain, placenta, lungs, skeletal muscles, kidneys, spleen, thymus, prostate, testis, ovaries, small intestine, colon, and leukocyte) was hybridized with P2XM cDNA.

(II) Homology search

Homology search of protein data bases revealed that the amino acid sequence of the gene of the present invention possessed homology to the ATP-gated ion channel (P2X) receptor family (Valera S., et al., Nature, 371: 516–519, 1994; Brake A. J., et al., Nature, 371: 519–523, 1994). In particular, it exhibited 80% homology to rat P2X6 (Collo G., et al., J. Neurosci., 16: 2495–2507, 1996) (see FIGS. 5 and 6).

Figures 4A, 4B:
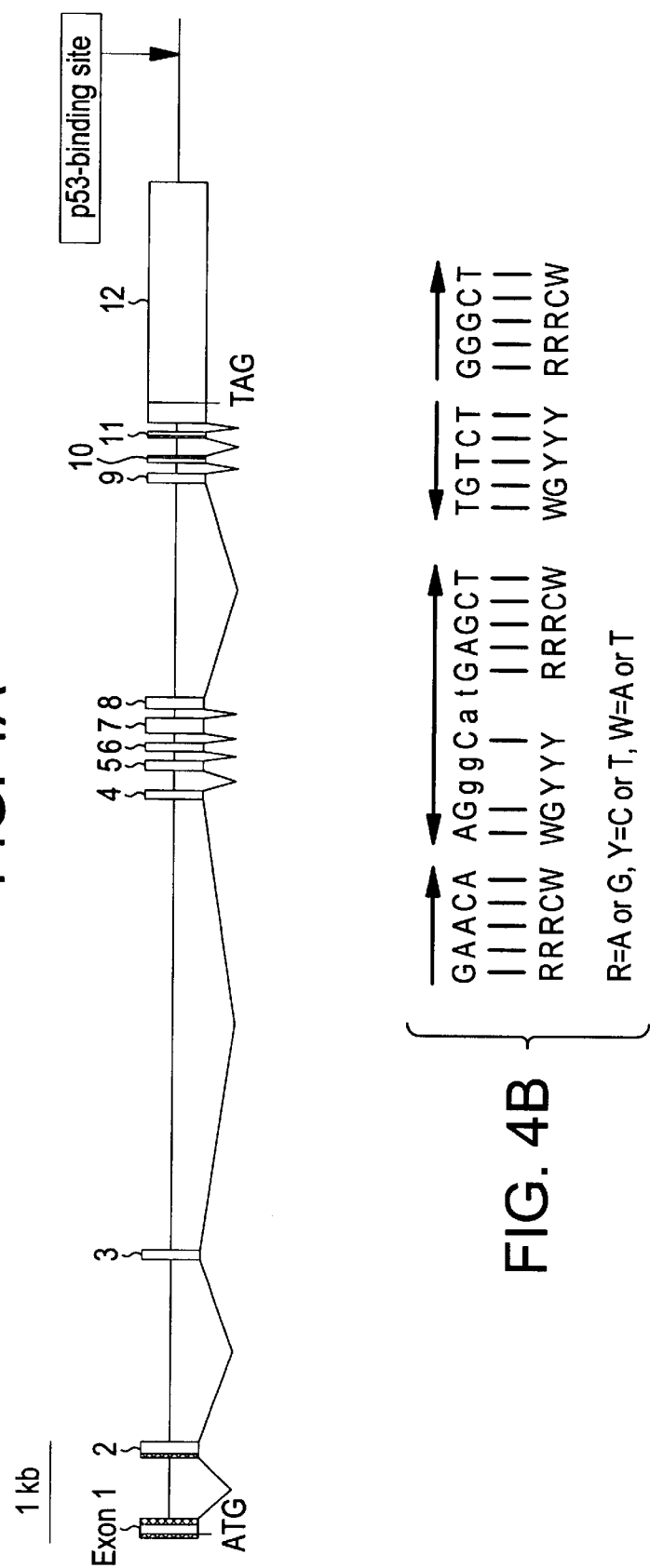
FIG. 4(a) shows locations of exons and a p53-binding site.
FIG. 4(b) shows a comparison between the p53-binding site of cosmid p53-191 and the consensus sequences of p53-binding sites.

FIGS. 3 and 4 depict the genome structure of the P2XM gene. FIG. 3 shows nucleotide sequences of exon-intron boundaries of the 191 gene. Exon and intron sequences are expressed in uppercase and lowercase letters, respectively. In FIG. 4(a), exon positions are drawn to scale according to their sizes, and exons are represented as numbered boxes. FIG. 4(b) shows a sequence comparison between the p53-binding site of cosmid p53-191 and the consensus sequences of p53-binding sites. Each arrow shows the consensus sequence (pentamer) of p53-binding sites; sequences in uppercase letters agree with the consensus, whereas those in the lowercase letters disagree with the consensus. All the P2X receptor (P2X1–X6) family members contain two transmembrane domains (M1 and M2), a segment (H5) homologous to the H5 domain of voltage-gated K+ channel, N-glycosylation sites, and 11 cysteine residues conserved evolutionarily (see FIGS. 5 and 6).

FIGS. 5 and 6 show the amino acid sequences of various P2X receptors. In these figures, boxed amino acid residues indicate those conserved commonly among P2XM and rat P2X1-P2X7 receptors. Lines on top of the figures indicate regions of two conserved hydrophobic domains (M1 and M2) and the H5 domain. A star indicates a potential N-glycosylation site.

The amino acid sequence encoded by the gene of the present invention shares the basic features of the P2X receptor family, thus implying that the gene of the present invention is a new member belonging to the P2XM family.

(III) Structural analysis

Figure 11:
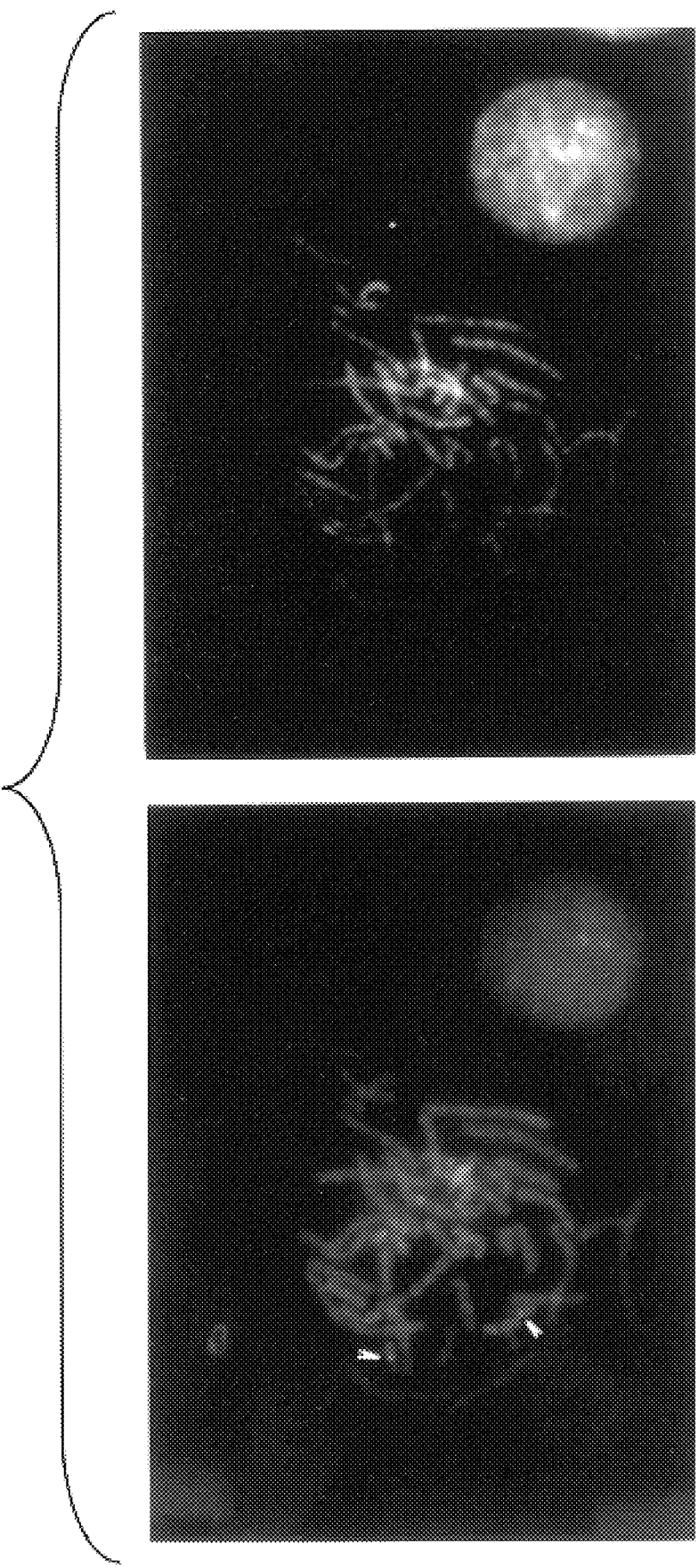
FIG. 11 are photos of the results of fluorescein in situ hybridization analysis.

Comparison between the above-mentioned cDNA and the corresponding genomic DNA sequence (p53-cos191) clarified the genome structure of this gene, including exon/intron boundaries and adjacent intron sequences (see FIG. 3). The gene consists of 12 exons spanning a 12-kb genome area (see FIG. 4a). The p53-tagged site is present about 1.6 kb downstream of the gene (see FIGS. 4a and b). By use of the fluorescein in situ hybridization (FISH) method with a probe of cosmid p53-cos191, the chromosomal location of the gene was detected at 22q11 (see FIG. 11; note that the specific hybridization signal was detected only at human chromosome band 22q11, but not on other chromosomes).

(IV) Alternative splicing in skeletal muscle

Figure 7:
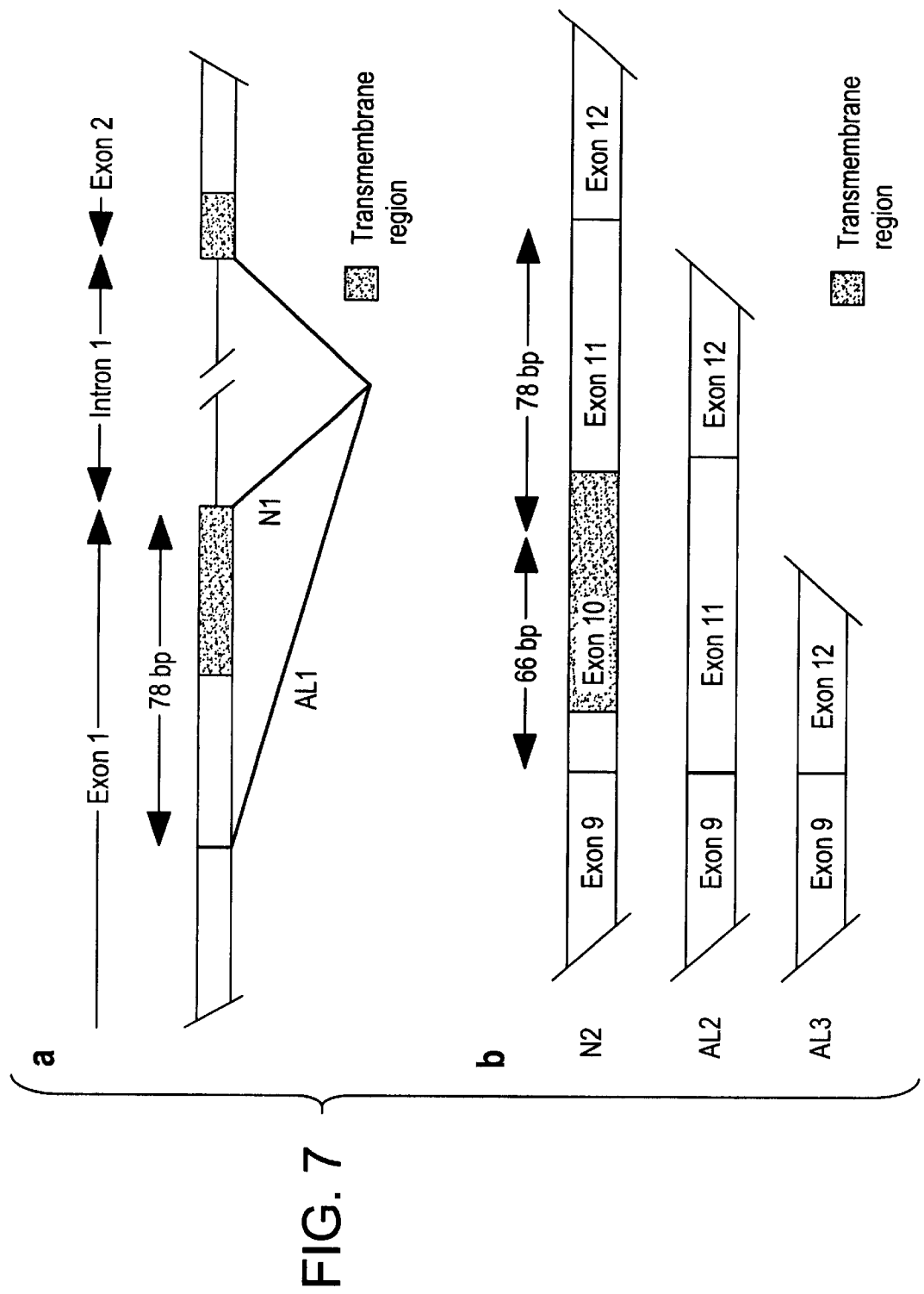
FIG. 7 depicts alternative splicing variants.

RT-PCR of RNA prepared from skeletal muscle, followed by direct DNA sequencing, confirmed 3 different in-frame transcripts (AL1, AL2, and AL3) resulting from alternative splicing, which lacked part of exon 1 from the donor site of exon 1 to 18 bases downstream, exon 10, and exons 10 and 11, respectively (see FIG. 7).

FIG. 7 shows a schematic figure of the alternative splicing. In the figure, the major RT-PCR amplified products from normal skeletal muscle are shown as N1 and N2, whereas the three types of variants are shown as AL1, AL2, and AL3.

Each of these alternative spliced transcripts lacked nucleotides multiples of 3, proving that the original reading frame intact was maintained.

As shown in FIGS. 3 and 4, exons 1–2 and exon 11 correspond to the transmembrane domains M1 and M2, respectively. In concert with the adjacent hydrophobic segment (H5) encoded by exon 10, the M1 and M2 domains are believed to form the ion pore and ion-binding site (Valera S., at al., Nature, 371: 516–519, 1994; Brake A. J., at al., Nature, 371: 519–523, 1994). From the structural point of view, these exons appear to encode biologically important domains.

(V) Expression of the alternatively spliced mRNAs in human cancer cell lines

Figure 8:
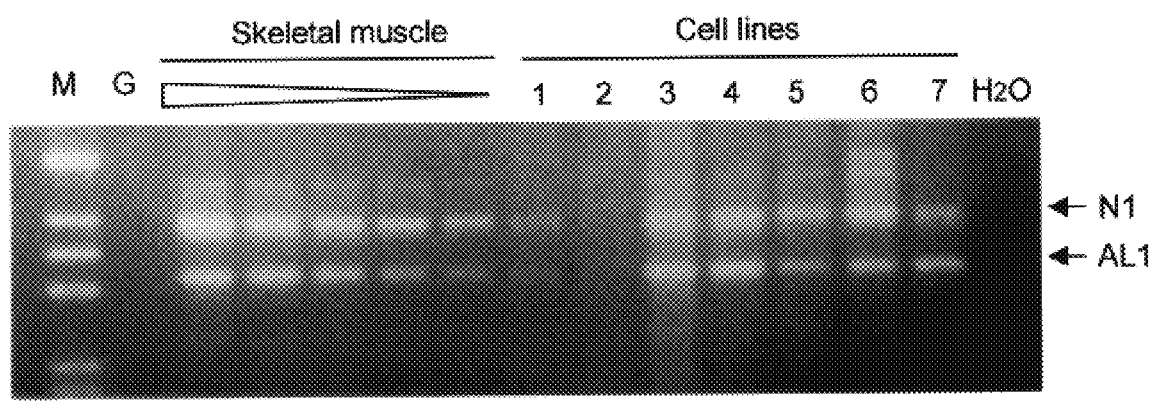
FIGS. 8–10 are photos of the results of RT-PCR analysis of splicing variants in muscle as well as in various cancer cell lines.
Figure 9:
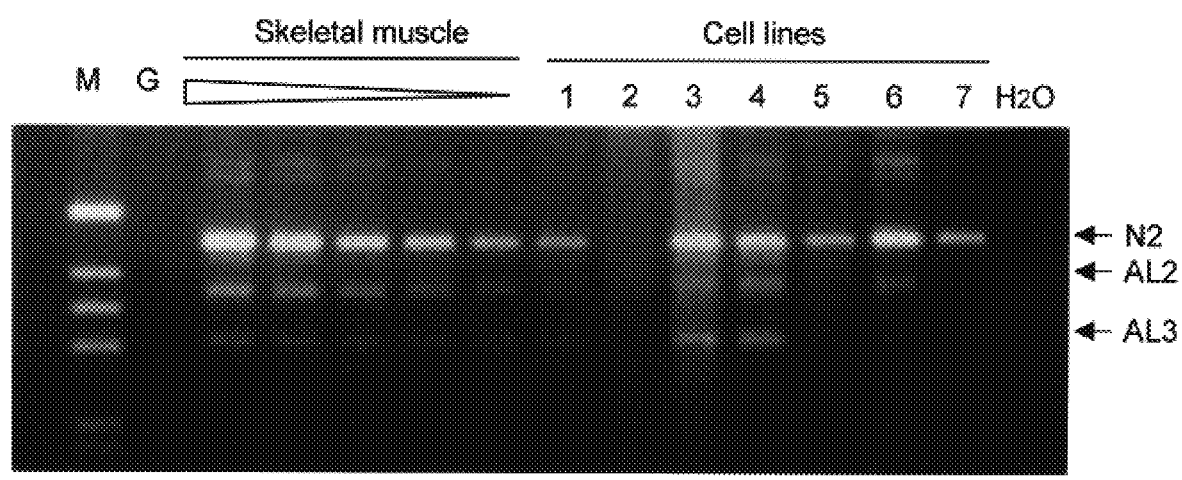
Figure 10:
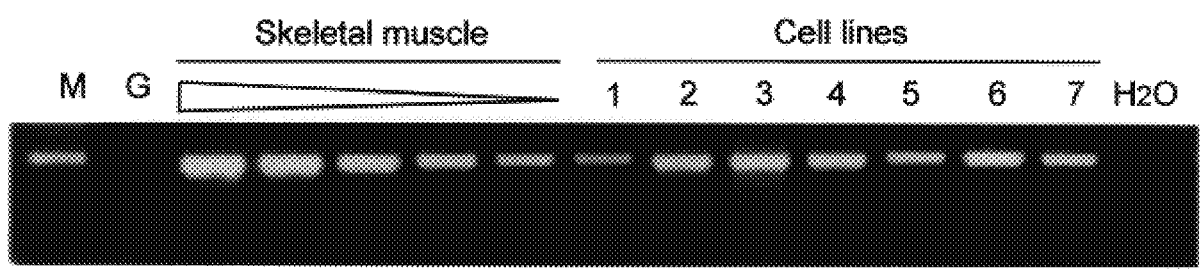

Recently, abnormal alternative splicing has been reported to somehow be involved in tumorigenicity, development of cancer, and/or its metastasis (Gunthert U., et al., Cell, 65: 13–24, 1991; Arch R., et al., Science (Washington DC), 257: 682–685, 1992). Therefore, mRNA levels of the alternative transcripts of the gene of the present invention in cell lines of 4 different rhabdomyosarcomas, 2 different osteosarcomas, and 1 liposarcoma were evaluated by RT-PCR analysis. The obtained results are shown in FIGS. 8–10. In the experiment, total RNA (200 ng) prepared from each cell line was analyzed as described above. To the lanes were applied rhabdomyosarcomas (cell line A204: lane 1; A673: lane 2; Hs729T: lane 3; and RD: lane 4), a liposarcoma (cell line SW872: lane5), and osteosarcomas (cell line NY: lane 6; Hu03N1: lane 7). Further, the results obtained by PCR amplification of diluted samples (1, 1:2, 1:4, 1:8, 1:16, 1:32) of the cDNA that had been prepared from skeletal muscle total RNA (200 ng) are also shown ("Skeletal muscles" lane).

FIGS. 8 and 9 show the results of N1, AL1, N2, AL2, and AL3, whose PCR products are of sizes 392, 314, 450, 384, and 306 bp, respectively. Note that amounts of RNA templates used for the above analysis were normalized with respect to PCR amplification of GAPDH, and thus all the samples applied showed similar levels of the GAPDH signal (FIG. 10).

The obtained results show that expression of the gene of the present invention decreased remarkably in one rhabdomyosarcoma (A673) among the 7 cell lines. In addition, the following findings of alternative splicing were observed with these cell lines: the profiles of transcripts lacking exon 10 and exons 10–11 in the cancer cell lines were similar to that in normal skeletal muscle; on the other hand, as compared with a relatively low level of the transcript variant lacking exon 1 in normal skeletal muscle, relatively high levels of the transcript were observed with one rhabdomyosarcoma (RD) and one osteosarcoma (Hu03N1).

(VI) Discussion

By means of the present invention, a new p53-inducible gene, a new member belonging to P2X family encoding ATP-gated ion channels, was isolated. The p53-binding site was located 1.6 kb downstream of the above gene, as revealed by sequencing the entire fragment of the cosmid DNA insert that also contained the above gene. Previously, the functional p53-binding sites of the genes regulated by p53 have been all located within their introns or promoter regions. However, in the case of the gene of the present invention, the functional p53-binding site was located downstream of the gene. These results suggest that the p53-binding site may work as an enhancer sequence.

The amino acid sequence deduced from the cDNA of the present invention showed homology to the P2X receptor family members, particularly to rat P2X6 (80% homology). However, rat P2X6 mRNA is distributed widely over the brain, whereas the gene of the present invention was specifically expressed only in skeletal muscle. Hence, the gene of the present invention is unlikely to be the human counterpart of rat P2X6. The P2X receptor is classified in the group of ATP-gated ion channels, and is believed to function as a mediator for extracellular ATP-inducible biological activity, such as cell death and synaptic transmission (Zheng L. M., et al., J. Cell Biol., 113: 279–288, 1991; Zoeteweij J. P., et al., Biochem. J., 288: 207–213, 1992; Kennedy C., et al., Nature, 377: 385–386, 1995). In addition, the gene of the present invention and that of a partial cDNA called RP-2 exhibit homology at the level of amino acid sequences. RP-2 was isolated by subtractive hybridization of mRNAs in rat thymocytes undergoing apoptosis induced by gamma-irradiation (Owens G. P., et al., Mol. Cell. Biol., 11: 4177–4188, 1991). Upon increasing intracellular Calcium concentrations, ATP induces death of thymocytes, hepatocytes, and various types of lymphocyte cell lines. These phenomena imply that the gene of the present invention is closely involved in p53-dependent apoptosis of skeletal muscle, possibly mediated through extracellular ATP.

Northern blot analysis revealed the presence of the 3.6-kb transcript in skeletal muscle. The expression level of the transcript decreased remarkably in one of the 4 rhabdomyosarcoma cell lines. Furthermore, even though an expression level of the spliced variant transcript lacking part of exon 1 encoding part of transmembrane domain M1 was a minor transcript in normal skeletal muscle, the expression level was relatively high in two of the remaining cancer cell lines. Notably, the ratio of the abnormal transcripts resulting from alternative splicing was relatively high in the cancer cell lines tested; and thus it is important to clarify the biological significance of the observed heterogeneity at the amino-terminal region. Moreover, in various cancer including rhabdomyosarcoma, there have been reports of deletion at the chromosomal location 22q11 where the gene of the present invention is present (Newsham I., et al., Genomics, 19: 433–440, 1994; Schofield D. E., et al., Genes Chromosom. Cancer, 15: 10–17, 1996; Biegel J. A., et al., Genes Chromosom. Cancer, 16: 94–105, 1996). These results suggest that the gene of the present invention may be a tumor suppressor gene present in this region.

INDUSTRIAL APPLICABILITY

Cloning of the functional p53-tagged site from the human genome led to isolation of a new gene inducible by wild-type p53. The DNA sequence of the cDNA contains an open reading frame encoding a peptide of 431 amino acid residues that has homology to the major characteristics of the members of P2X receptor family (ATP-gated ion channels). The peptide has also homology to RP-2, a gene that can be activated in the thymus undergoing induced programmed cell death. The gene of the present invention is expressed mainly in skeletal muscle, was named P2XM (P2X specifically expressed in skeletal muscle), and is considered to be involved in suppression of cell growth and/or apoptosis of skeletal muscle.

Expression of the transcript in one of the 4 rhabdomyosarcoma cell lines was remarkably suppressed. Furthermore, levels of the splicing variant transcript lacking part of exon 1 encoding transmembrane domain M1, which was a minor species in normal muscle, were relatively high in two out of the seven cancer cell lines tested, implying that the production rate of such altered transcripts drastically increases in cancer cell lines. Further, the gene of the present invention was located at chromosome band 22q11, which is known to undergo deletion in rhabdoid tumors.

By means of the gene of the present invention, a new human gene transcriptionally regulated specifically by the tumor suppressor gene p53 is provided. By use of the gene, its expression in various tissue can be detected, and the structure and function of the product encoded by the gene can be analyzed. Also, the gene product can be manufactured by means of gene engineering techniques. Taken together, these findings lead to further understanding of tumorigenicity, development of cancer, its metastasis, etc., and provide useful techniques for the diagnosis, prevention, treatment, etc. of cancer.

What is claimed is:

1. An isolated nucleic acid molecule encoding a human skeletal muscle-specific receptor comprising a nucleotide sequence encoding the amino acid sequence shown in SEQ ID NO:3.

2. The isolated nucleic acid molecule according to claim 1, wherein said isolated nucleic acid molecule comprises a nucleotide sequence shown in SEQ ID NO:1.

3. An isolated nucleic acid molecule that specifically hybridizes, under hybridization wash conditions of 50° C. in 0.1 x SSC and 0.1% SDS, to the complement of the sequence set forth in SEQ ID NO:2, wherein said nucleic acid encodes a human skeletal muscle-specific receptor.

* * * * *

SEQUENCE LISTING

<160> NUMBER OF SEQ ID NOS: 9

<210> SEQ ID NO: 1
<211> LENGTH: 1293
<212> TYPE: DNA
<213> ORGANISM: Human

<400> SEQUENCE: 1

```
atgggctccc cagggctac gacaggctgg gggcttctgg attataagac ggagaagtat      60
gtgatgacca ggaactggcg ggtgggcgcc ctgcagaggc tgctgcagtt tgggatcgtg     120
gtctatgtgg tagggtgggc gctcctcgcc aaaaaaggct accaggagcg ggacctggaa     180
ccccagtttt ccatcatcac caaactcaaa ggggtttccg tcactcagat caaggagctt     240
ggaaaccggc tgtgggatgt ggccgacttc gtgaagccac ctcagggaga gaacgtgttc     300
ttcttggtga ccaacttcct tgtgacgcca gcccaagttc agggcagatg cccagagcac     360
ccgtccgtcc cactggctaa ctgctgggtc gacgaggact gccccgaagg ggagggaggc     420
```

-continued

```
acacacagcc acggtgtaaa aacaggccag tgtgtggtgt tcaatgggac ccacaggacc    480
tgtgagatct ggagttggtg ccccgtggag agtggcgttg tgcctcgag gccctgctg    540
gcccaggccc agaacttcac actgttcatc aaaaacacag tcaccttcag caagttcaac    600
ttctctaagt ccaatgcctt ggagacctgg gaccccacct attttaagca ctgccgctat    660
gaaccacaat tcagcccta ctgtcccgtg ttccgcattg ggacctcgt ggccaaggct    720
ggagggacct tcgaggacct ggcgttgctg ggtggctctg taggcatcag agttcactgg    780
gattgtgacc tggacaccgg ggactctggc tgctggcctc actactcctt ccagctgcag    840
gagaagagct acaacttcag acagccact cactggtggg agcaaccggg tgtggaggcc    900
cgcaccctgc tcaagctcta tggaatccgc ttcgacatcc tcgtcaccgg gcaggcaggg    960
aagttcgggc tcatccccac ggccgtcaca ctgggcaccg ggcagcttg gctgggcgtg    1020
gtcaccttt tctgtgacct gctactgctg tatgtggata gagaagccca tttctactgg    1080
aggacaaagt atgaggaggc caaggccccg aaagcaaccg ccaactctgt gtggagggag    1140
ctggcccttg catcccaagc ccgactggcc gagtgcctca acggagctc agcacctgca    1200
cccacggcca ctgctgctgg gagtcagaca cagacaccag gatggccctg tccaagttct    1260
gacacccact tgccaaccca ttccgggagc ctg    1293
```

<210> SEQ ID NO: 2
<211> LENGTH: 1697
<212> TYPE: DNA
<213> ORGANISM: Human
<220> FEATURE:
<221> NAME/KEY: CDS
<222> LOCATION: (46)..(1338)

<400> SEQUENCE: 2

```
ctgccatgct gactcatgtg cccgcagcta gcaggagctg gcagc atg ggc tcc cca    57
                                                  Met Gly Ser Pro
                                                    1 ggg gct acg aca ggc tgg ggg ctt ctg gat tat aag acg gag aag tat   105
Gly Ala Thr Thr Gly Trp Gly Leu Leu Asp Tyr Lys Thr Glu Lys Tyr
  5                  10                  15                  20 gtg atg acc agg aac tgg cgg gtg ggc gcc ctg cag agg ctg ctg cag   153
Val Met Thr Arg Asn Trp Arg Val Gly Ala Leu Gln Arg Leu Leu Gln
                 25                  30                  35 ttt ggg atc gtg gtc tat gtg gta ggg tgg gcg ctc ctc gcc aaa aaa   201
Phe Gly Ile Val Val Tyr Val Val Gly Trp Ala Leu Leu Ala Lys Lys
             40                  45                  50 ggc tac cag gag cgg gac ctg gaa ccc cag ttt tcc atc atc acc aaa   249
Gly Tyr Gln Glu Arg Asp Leu Glu Pro Gln Phe Ser Ile Ile Thr Lys
 55                  60                  65 ctc aaa ggg gtt tcc gtc act cag atc aag gag ctt gga aac cgg ctg   297
Leu Lys Gly Val Ser Val Thr Gln Ile Lys Glu Leu Gly Asn Arg Leu
        70                  75                  80 tgg gat gtg gcc gac ttc gtg aag cca cct cag gga gag aac gtg ttc   345
Trp Asp Val Ala Asp Phe Val Lys Pro Pro Gln Gly Glu Asn Val Phe
 85                  90                  95                 100 ttc ttg gtg acc aac ttc ctt gtg acg cca gcc caa gtt cag ggc aga   393
Phe Leu Val Thr Asn Phe Leu Val Thr Pro Ala Gln Val Gln Gly Arg
                105                 110                 115 tgc cca gag cac ccg tcc gtc cca ctg gct aac tgc tgg gtc gac gag   441
Cys Pro Glu His Pro Ser Val Pro Leu Ala Asn Cys Trp Val Asp Glu
            120                 125                 130
```

-continued

| | |
|---|---|
| gac tgc ccc gaa ggg gag gga ggc aca cac agc cac ggt gta aaa aca<br>Asp Cys Pro Glu Gly Glu Gly Gly Thr His Ser His Gly Val Lys Thr<br>           135                        140                       145 | 489 |
| ggc cag tgt gtg gtg ttc aat ggg acc cac agg acc tgt gag atc tgg<br>Gly Gln Cys Val Val Phe Asn Gly Thr His Arg Thr Cys Glu Ile Trp<br>150                          155                       160 | 537 |
| agt tgg tgc ccc gtg gag agt ggc gtt gtg ccc tcg agg ccc ctg ctg<br>Ser Trp Cys Pro Val Glu Ser Gly Val Val Pro Ser Arg Pro Leu Leu<br>165                       170                      175                180 | 585 |
| gcc cag gcc cag aac ttc aca ctg ttc atc aaa aac aca gtc acc ttc<br>Ala Gln Ala Gln Asn Phe Thr Leu Phe Ile Lys Asn Thr Val Thr Phe<br>           185                       190                      195 | 633 |
| agc aag ttc aac ttc tct aag tcc aat gcc ttg gag acc tgg gac ccc<br>Ser Lys Phe Asn Phe Ser Lys Ser Asn Ala Leu Glu Thr Trp Asp Pro<br>                200                       205                    210 | 681 |
| acc tat ttt aag cac tgc cgc tat gaa cca caa ttc agc ccc tac tgt<br>Thr Tyr Phe Lys His Cys Arg Tyr Glu Pro Gln Phe Ser Pro Tyr Cys<br>           215                       220                      225 | 729 |
| ccc gtg ttc cgc att ggg gac ctc gtg gcc aag gct gga ggg acc ttc<br>Pro Val Phe Arg Ile Gly Asp Leu Val Ala Lys Ala Gly Gly Thr Phe<br>230                          235                       240 | 777 |
| gag gac ctg gcg ttg ctg ggt ggc tct gta ggc atc aga gtt cac tgg<br>Glu Asp Leu Ala Leu Leu Gly Gly Ser Val Gly Ile Arg Val His Trp<br>245                       250                       255              260 | 825 |
| gat tgt gac ctg gac acc ggg gac tct ggc tgc tgg cct cac tac tcc<br>Asp Cys Asp Leu Asp Thr Gly Asp Ser Gly Cys Trp Pro His Tyr Ser<br>                265                       270                    275 | 873 |
| ttc cag ctg cag gag aag agc tac aac ttc agg aca gcc act cac tgg<br>Phe Gln Leu Gln Glu Lys Ser Tyr Asn Phe Arg Thr Ala Thr His Trp<br>           280                       285                    290 | 921 |
| tgg gag caa ccg ggt gtg gag gcc cgc acc ctg ctc aag ctc tat gga<br>Trp Glu Gln Pro Gly Val Glu Ala Arg Thr Leu Leu Lys Leu Tyr Gly<br>                295                       300                    305 | 969 |
| atc cgc ttc gac atc ctc gtc acc ggg cag gca ggg aag ttc ggg ctc<br>Ile Arg Phe Asp Ile Leu Val Thr Gly Gln Ala Gly Lys Phe Gly Leu<br>310                          315                       320 | 1017 |
| atc ccc acg gcc gtc aca ctg ggc acc ggg gca gct tgg ctg ggc gtg<br>Ile Pro Thr Ala Val Thr Leu Gly Thr Gly Ala Ala Trp Leu Gly Val<br>325                          330                       335              340 | 1065 |
| gtc acc ttt ttc tgt gac ctg cta ctg ctg tat gtg gat aga gaa gcc<br>Val Thr Phe Phe Cys Asp Leu Leu Leu Leu Tyr Val Asp Arg Glu Ala<br>                345                       350                    355 | 1113 |
| cat ttc tac tgg agg aca aag tat gag gag gcc aag gcc ccg aaa gca<br>His Phe Tyr Trp Arg Thr Lys Tyr Glu Glu Ala Lys Ala Pro Lys Ala<br>           360                       365                    370 | 1161 |
| acc gcc aac tct gtg tgg agg gag ctg gcc ctt gca tcc caa gcc cga<br>Thr Ala Asn Ser Val Trp Arg Glu Leu Ala Leu Ala Ser Gln Ala Arg<br>                375                       380                    385 | 1209 |
| ctg gcc gag tgc ctc aga cgg agc tca gca cct gca ccc acg gcc act<br>Leu Ala Glu Cys Leu Arg Arg Ser Ser Ala Pro Ala Pro Thr Ala Thr<br>390                          395                       400 | 1257 |
| gct gct ggg agt cag aca cag aca cca gga tgg ccc tgt cca agt tct<br>Ala Ala Gly Ser Gln Thr Gln Thr Pro Gly Trp Pro Cys Pro Ser Ser<br>405                          410                       415              420 | 1305 |
| gac acc cac ttg cca acc cat tcc ggg agc ctg tagccgttcc ctgctggttg<br>Asp Thr His Leu Pro Thr His Ser Gly Ser Leu<br>                     425                       430 | 1358 |
| agagttgggg gctgggaagg gcggggccct gcctggggat ttcaaggatg aggccccagc | 1418 |
| atggaggatt ggggggtagaa ttccacccct gaaccccagc aaacagtccc tcccctgact | 1478 |

-continued

```
cccaccttgg tagggtgctg cctcagggag ccataaaagt cggctgtgtt ttgagacggc    1538
gacagaacct gacccgtgga gactgggaga gcccagcagg cacctgtatt gcagggctcc    1598
gactgcatgt ggcaggggct cctgctgcgt ctgggcctga aggtctctct cccagtgctc    1658
tgtccccagt gttcctagca gaggtatgct taccagctg                           1697
```

<210> SEQ ID NO: 3
<211> LENGTH: 431
<212> TYPE: PRT
<213> ORGANISM: Human

<400> SEQUENCE: 3

```
Met Gly Ser Pro Gly Ala Thr Thr Gly Trp Gly Leu Leu Asp Tyr Lys
  1               5                  10                  15

Thr Glu Lys Tyr Val Met Thr Arg Asn Trp Arg Val Gly Ala Leu Gln
             20                  25                  30

Arg Leu Leu Gln Phe Gly Ile Val Val Tyr Val Gly Trp Ala Leu
         35                  40                  45

Leu Ala Lys Lys Gly Tyr Gln Glu Arg Asp Leu Glu Pro Gln Phe Ser
     50                  55                  60

Ile Ile Thr Lys Leu Lys Gly Val Ser Val Thr Gln Ile Lys Glu Leu
 65                  70                  75                  80

Gly Asn Arg Leu Trp Asp Val Ala Asp Phe Val Lys Pro Pro Gln Gly
                 85                  90                  95

Glu Asn Val Phe Phe Leu Val Thr Asn Phe Leu Val Thr Pro Ala Gln
            100                 105                 110

Val Gln Gly Arg Cys Pro Glu His Pro Ser Val Pro Leu Ala Asn Cys
        115                 120                 125

Trp Val Asp Glu Asp Cys Pro Glu Gly Glu Gly Thr His Ser His
    130                 135                 140

Gly Val Lys Thr Gly Gln Cys Val Val Phe Asn Gly Thr His Arg Thr
145                 150                 155                 160

Cys Glu Ile Trp Ser Trp Cys Pro Val Glu Ser Gly Val Val Pro Ser
                165                 170                 175

Arg Pro Leu Leu Ala Gln Ala Gln Asn Phe Thr Leu Phe Ile Lys Asn
            180                 185                 190

Thr Val Thr Phe Ser Lys Phe Asn Phe Ser Lys Ser Asn Ala Leu Glu
        195                 200                 205

Thr Trp Asp Pro Thr Tyr Phe Lys His Cys Arg Tyr Glu Pro Gln Phe
    210                 215                 220

Ser Pro Tyr Cys Pro Val Phe Arg Ile Gly Asp Leu Val Ala Lys Ala
225                 230                 235                 240

Gly Gly Thr Phe Glu Asp Leu Ala Leu Leu Gly Gly Ser Val Gly Ile
                245                 250                 255

Arg Val His Trp Asp Cys Asp Leu Asp Thr Gly Asp Ser Gly Cys Trp
            260                 265                 270

Pro His Tyr Ser Phe Gln Leu Gln Glu Lys Ser Tyr Asn Phe Arg Thr
        275                 280                 285

Ala Thr His Trp Trp Glu Gln Pro Gly Val Glu Ala Arg Thr Leu Leu
    290                 295                 300

Lys Leu Tyr Gly Ile Arg Phe Asp Ile Leu Val Thr Gly Gln Ala Gly
305                 310                 315                 320

Lys Phe Gly Leu Ile Pro Thr Ala Val Thr Leu Gly Thr Gly Ala Ala
                325                 330                 335
```

```
Trp Leu Gly Val Val Thr Phe Phe Cys Asp Leu Leu Leu Tyr Val
            340                 345                 350

Asp Arg Glu Ala His Phe Tyr Trp Arg Thr Lys Tyr Glu Glu Ala Lys
            355                 360                 365

Ala Pro Lys Ala Thr Ala Asn Ser Val Trp Arg Glu Leu Ala Leu Ala
            370                 375                 380

Ser Gln Ala Arg Leu Ala Glu Cys Leu Arg Arg Ser Ser Ala Pro Ala
385                 390                 395                 400

Pro Thr Ala Thr Ala Ala Gly Ser Gln Thr Gln Thr Pro Gly Trp Pro
                    405                 410                 415

Cys Pro Ser Ser Asp Thr His Leu Pro Thr His Ser Gly Ser Leu
                    420                 425                 430

<210> SEQ ID NO: 4
<211> LENGTH: 18
<212> TYPE: DNA
<213> ORGANISM: Human

<400> SEQUENCE: 4
agccactcac tggtggga                                                    18

<210> SEQ ID NO: 5
<211> LENGTH: 20
<212> TYPE: DNA
<213> ORGANISM: Human

<400> SEQUENCE: 5
cccggtgacg aggatgtcga                                                  20

<210> SEQ ID NO: 6
<211> LENGTH: 20
<212> TYPE: DNA
<213> ORGANISM: Human

<400> SEQUENCE: 6
gttccttgtg gagccggagc                                                  20

<210> SEQ ID NO: 7
<211> LENGTH: 21
<212> TYPE: DNA
<213> ORGANISM: Human

<400> SEQUENCE: 7
ggtacaagac agtgacaggt c                                                21

<210> SEQ ID NO: 8
<211> LENGTH: 22
<212> TYPE: DNA
<213> ORGANISM: Human

<400> SEQUENCE: 8
caactacatg gtttacatgt tc                                               22

<210> SEQ ID NO: 9
<211> LENGTH: 18
<212> TYPE: DNA
<213> ORGANISM: Human

<400> SEQUENCE: 9
gccagtggac tccacgac                                                    18
```